(12) United States Patent
Liaw et al.

(10) Patent No.: US 9,157,849 B2
(45) Date of Patent: Oct. 13, 2015

(54) CHANGED OPTICAL PATH MEASURING DEVICE FOR COMPONENT CONCENTRATION OF WATER AND MEASURING METHOD THEREOF

(71) Applicants: National Central University, Taoyuan (TW); Industrial Technology Research Institute, Hsinchu (TW)

(72) Inventors: Shu-Liang Liaw, Taipei (TW); Chien-Ku Chen, Taichung (TW); Hsin-Yi Wang, New Taipei (TW); Yang-Yu Lin, Tainan (TW); Chen-Hua Chu, Hsinchu County (TW); Chih-Chung Chan, Tainan (TW)

(73) Assignees: National Central University, Hsinchu (TW); Industrial Technology Research Institute, Hsinchu (TW)

( * ) Notice: Subject to any disclaimer, the term of this patent is extended or adjusted under 35 U.S.C. 154(b) by 0 days.

(21) Appl. No.: 14/546,308

(22) Filed: Nov. 18, 2014

(65) Prior Publication Data

US 2015/0070702 A1    Mar. 12, 2015

Related U.S. Application Data

(62) Division of application No. 13/727,804, filed on Dec. 27, 2012, now Pat. No. 8,941,827.

(30) Foreign Application Priority Data

Dec. 29, 2011 (TW) ............................. 100149661 A

(51) Int. Cl.
    *G01N 1/10* (2006.01)
    *G01N 21/17* (2006.01)
    (Continued)

(52) U.S. Cl.
    CPC ............ *G01N 21/17* (2013.01); *G01N 21/0303* (2013.01); *G01N 21/31* (2013.01)

(58) Field of Classification Search
    CPC .................. G01N 21/03; G01N 15/06; G01N 2021/0346
    USPC .................. 356/244, 246, 432–440; 250/900; 280/830
    See application file for complete search history.

(56) References Cited

U.S. PATENT DOCUMENTS

| 4,257,708 A | 3/1981 | Fukuda |
| 5,224,634 A | 7/1993 | Graham |

(Continued)

FOREIGN PATENT DOCUMENTS

| CN | 2859515 Y | 1/2007 |
| JP | 57142546 A2 | 9/1982 |

(Continued)

OTHER PUBLICATIONS

Office Action, Taiwanese Patent Application No. 20110149661, dated May 14, 2014.

*Primary Examiner* — Hoa Pham
(74) *Attorney, Agent, or Firm* — Volpe and Koenig, P.C.

(57) ABSTRACT

Measuring device of the present invention includes a plurality of measuring sites for generating a plurality of optical paths and various dilutions. The range for concentration measurement and the measurement accuracy are enhanced due to the plurality of optical path length, and the interference on the measurement ranges and results caused by the concentration or the turbidity of suspended solid is reduced and removed by water sample dilution, and thus the characteristic wavelengths of the components in the water are measured. Next, the information of spectrum database is used to determine the ingredients which may exist in the water (qualitative analysis), and UV-VIS-NIR absorbance spectrum analysis is used to obtain the concentration of the respective ingredients in the water at the same time (quantitative analysis).

4 Claims, 13 Drawing Sheets

(51) Int. Cl.
  *G01N 21/03* (2006.01)
  *G01N 21/31* (2006.01)

(56) References Cited

U.S. PATENT DOCUMENTS

| | | | |
|---|---|---|---|
| 5,876,674 A | 3/1999 | Dosoretz et al. | |
| 6,249,345 B1 * | 6/2001 | Kraack et al. | 356/246 |
| 8,493,559 B2 * | 7/2013 | Harvard | 356/246 |
| 2009/0141280 A1 | 6/2009 | Lam et al. | |
| 2009/0145202 A1 | 6/2009 | Tokhtuev et al. | |
| 2009/0263907 A1 | 10/2009 | Asano et al. | |
| 2013/0314697 A1 | 11/2013 | Voit et al. | |

FOREIGN PATENT DOCUMENTS

| | | |
|---|---|---|
| JP | 357208440 A | 12/1982 |
| TW | 201024726 A | 7/2010 |
| TW | 201111763 A | 4/2011 |
| TW | 201124711 A | 7/2011 |
| TW | 201124712 A | 7/2011 |
| TW | M413120 Y | 10/2011 |

* cited by examiner

CHANGED OPTICAL PATH MEASURING DEVICE FOR COMPONENT CONCENTRATION OF WATER AND MEASURING METHOD THEREOF

CROSS REFERENCE TO RELATED APPLICATION

This application is a Divisional of U.S. application Ser. No. 13/727,804 filed Dec. 27, 2012, which claims the benefit of Taiwan Patent Application No. 100149661, filed on Dec. 29, 2011, in the Intellectual Property Office of Republic of China, the disclosure of which is incorporated by reference as if fully set forth herein.

FIELD OF THE INVENTION

The present invention relates to a measuring device and a measuring method, in particular, to a device and a method for measuring water quality by ultraviolet-visible-near infrared (UV-VIS-NIR) absorbance spectrum. The measuring device has a plurality of measuring sites for generating a plurality of optical path length. The measuring method can reduce and remove the concentration or turbidity of suspended solid which cause the interference on the measurement ranges and results via various dilutions.

BACKGROUND OF THE INVENTION

In general, the measurement of the chemical oxygen demand for water commonly uses a potassium bichromate method which must add chemicals and an electrochemical measurement method which must use a contract electrode. However, the chemicals added in the potassium bichromate method and the contract electrode used in the electrochemical measurement method will influence the reaction time and the stability of the system, and cause the issues of hardly maintenance and operation and poor measuring quality.

In addition, the commercial instruments measuring the suspended solid concentration utilize optical measurement scheme to perform measurements the single-wavelength absorbance to perform analysis. However, the analysis of the single-wavelength absorbance is not suitable for the measurement of variety of different particle sizes of suspended particulates.

The heavy metal mainly comes from a traditional industry, an electroplating industry and a printed circuit board (PCB) industry. The heavy metal pollution such as a copper, a nickel, an iron, a zinc, a chromium and a cadmium pollution, is more harmful than other organic pollution because the heavy metal or the metal compound thereof is not easy to degrade or reduce its concentration by a physical, a chemical or a biologic reaction in the nature. In the wastewater treatment system, the excessively high heavy metal concentration in the waste water will poison the microbe which causes the treatment system unable to function normally. Therefore, how to control the concentration of the heavy metal in the water to further enhance the treatment effectiveness, and to reduce the total quantity of the heavy metal for protecting the ecology of the water is an important topic.

The study of the heavy metal measurement can be divided into three technologies, which are the developer addition technology, the improvement and development of the analysis equipment technology, and the biochip technology. In developer addition technology, the method in this technique can measure only one type of metal, and its reagents cost expensive. Moreover, the developer addition technology has issues on waste liquid generation and treatment. In the improvement and development of the analysis equipment technique, the equipments cost expensive and must consume massive amount of water to perform analysis. The method of the equipment also needs to gauge the range of the concentration by artificial way to establish a calibration curve for every kinds of heavy metal which results in a relatively longer measuring time and causes artificial inaccuracy. In biochip technique, the measurement thereof can be performed more accuracy for copper ion in present. However, the biochip technique cannot obtain a plurality of the data of the heavy metal concentration simultaneously and would be interfered by the particles easily.

U.S. Pat. No. 5,224,634 discloses that a chelating resin having a specific functional group makes the water sample through the open chelation column chromatography to detect the transition element or the rare element in the water sample. U.S. Patent Publication No. 2009/0263907 A1 discloses using a reagent colorimetry method to measure the heavy metal concentration in the water sample such as waste water in the environment. However, these two patents use developer addition and chelating agent respectively which are combined with heavy metal to make the aqueous solution produce color. Then the two patents determine the concentration of the heavy metal according to the depth of color, which causes secondary pollution to the environment.

In wastewater treatment, the heavy metals are commonly measured by the fast heavy metal measurement detector or atomic absorption (AA) spectroscope. However, the detector or spectroscope cannot obtain real-time, accurate and effective monitoring information to satisfy the demands for control. Therefore, it is an important topic to develop a measuring device and method for measuring the heavy metal by various dilutions and scans to remove suspended solid (SS) and chemical oxygen demand (COD), so as to obtain the concentration of the heavy metal such as copper, nickel, iron, zinc and chromium.

In the past, the most optical schemes used in measuring the water components, such as COD, ammonia, heavy metal and SS, can measure one item only, and the measuring range and accuracy thereof are typically limited by the turbidity and SS in the water. The most of the conventional measuring methods utilize a single wavelength or select a better wavelength in the various estimated results to measure the component in the water. Due to the component will interfere, compete and shelter to each other in every components when there are many water component, such kind of measurement technique will not obtain a better measuring result.

It is therefore attempted by the applicant to deal with the above situation encountered in the prior art.

SUMMARY OF THE INVENTION

In order to devise the elimination of spectral interference generated by the SS and the COD, and measure the concentration of various kind of water components simultaneously. According to the Beer-Lamber principle, the present invention uses spectral scan to establish a measuring device and method, which obtaining the concentration of various kinds of heavy metals simultaneously and a heavy metal real-time monitoring system is formed by this measure technique and a batch measuring equipment.

In a measuring device, including: a tank, a supporting portion, a vehicle, a first light source and a first measuring element. The tank has a first and a second laterals including a first and a second virtual extensions respectively, for filling therein a water wherein the first and the second laterals are light-permeable and oppositely configured, and the first and the second virtual extensions intersects to form an angle. The supporting portion has at least one supporting frame connected to the tank. The vehicle has at least one moving device connected to the supporting portion for fixing the supporting portion and vertically moving the supporting portion. The first light source is configured outside the tank and generating a first light toward to the first lateral. The first measuring element is configured outside the tank and facing the second lateral for receiving the first light passing sequentially through the first lateral, the water and the second lateral to measure the water.

In a measuring device, including: a tank filled with a fluid sample. The tank has at least two optical paths for measuring a property of the fluid sample through the at least two optical paths.

In a fluid sample measuring process, including steps of: (a) measuring a change of a spectral intensity of the fluid sample to obtain an absorbance. (b) The absorbance is determined whether the absorbance falls in an error tolerance. If not, at least one of diluting the fluid sample and changing an optical length is/are performed. (c) The steps (a) and (b) are repeated until the absorbance falls in the error tolerance.

The above objectives and advantages of the present invention will become more readily apparent to those ordinarily skilled in the art after reviewing the following detailed descriptions.

EXPERIMENTAL MATERIALS AND METHODS

The present invention will now be described more specifically with reference to the following embodiments. It is to be noted that the following descriptions of preferred embodiments of this invention are presented herein for purposes of illustration and description only; it is not intended to be exhaustive or to be limited to the precise form disclosed.

Figure 1:
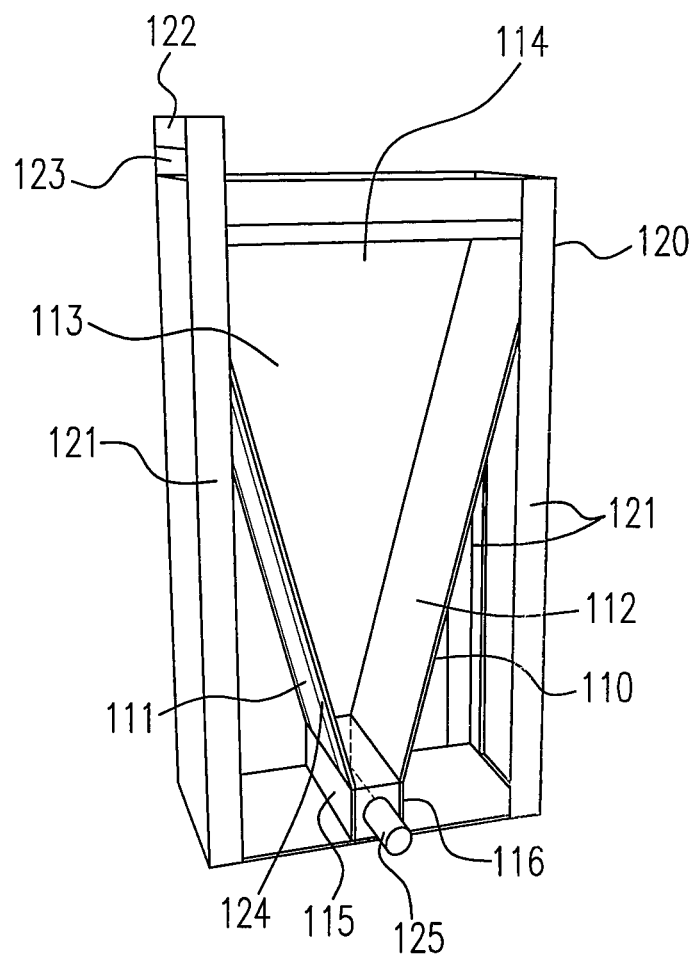
FIG. 1 shows the water tank structure of the present invention.

The measuring device according to the present invention includes a water tank and a vehicle for carrying the water tank. The structure of the water tank of the present invention is shown in FIG. 1, where the water tank 100 includes a tank 110, and the tank 110 can fills water and include a first lateral 111 and a second lateral 112. The first lateral 111 and second lateral 112 include a first and a second virtual extensions respectively, wherein the first lateral 111 and the second lateral 112 are oppositely configured and light-permeable. The first and the second virtual extensions are intersected and form an angle so that the tank 110 is formed as an inverted triangular prism. The light passing sequentially through the first lateral 111, the water and the second lateral 112 of the tank 110 forms a plurality of optical paths. The tank 110 further includes a third lateral 113 (a lateral facing toward the eye of the reader) and a fourth lateral 114 (a lateral far away from the eye of the reader). The third lateral 113 is light-permeable and connected to the first lateral 111 and the second lateral 112, and the fourth lateral 114 is light permeable, connected to the first lateral 111 and the second lateral 112 and parallel to the third lateral 113. The tank 110 further includes a fifth lateral 115 and a sixth lateral 116 parallel to each other. the fifth lateral 115 is connected with the first lateral 111, the sixth lateral 116 is connected with the second lateral 112, the intersection formed by the virtual extensions of the first lateral 111 and the second lateral 112 is situated between the fifth lateral 115 and the sixth lateral 116 (the embodiment in the present invention is "over"), the fifth lateral 115 and the sixth lateral 116 is connected with the bottom to form a cuboid, and the tank 110 has a smallest optical path of light between the fifth lateral 115 and the sixth lateral 116 which is 0.8 cm in the embodiment according to the present invention. The water tank 110 further includes a supporting portion 120 having at least one supporting frame 121 connected to the tank 110, the supporting portion 120 has an attachment point with the tank 110, and renders the tank 110 extending upward from the attachment point. The tank 110 further includes a freeing port 125 configured at the third lateral 113 of the cuboid to drain a clean water or a waste water out of the tank 110. The water tank 100 further includes an air tank 123 configured above the tank 110 and an opaque black tank 122 configured above the air tank 123, wherein the air tank 123 and the opaque black tank 122 acts as a calibration base for a light source intensity and a light sensor. The water tank further includes an ultrasonic device 124 configured on the outer wall (such as configured on the first lateral 111 of FIG. 1). When the tank 110 fills with fluid sample, the ultrasonic device 124 can clean the tank 100 and mix the fluid sample therein by utilizing various frequencies. The ultrasonic device 124 is a sonicator or an ultrasonic oscillator.

Figure 2A:
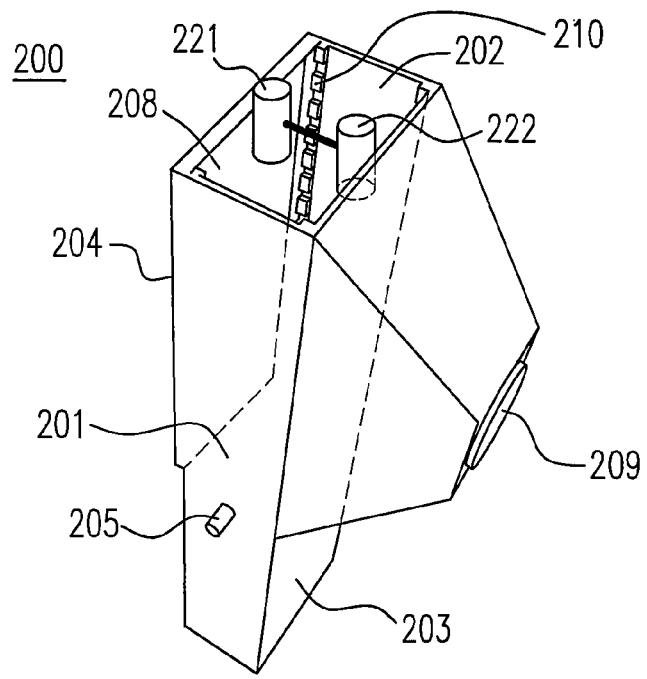
FIGS. 2(a) and 2(b) show the perspective schematic view and the back perspective view of the vehicle of the present invention.
Figure 2B:
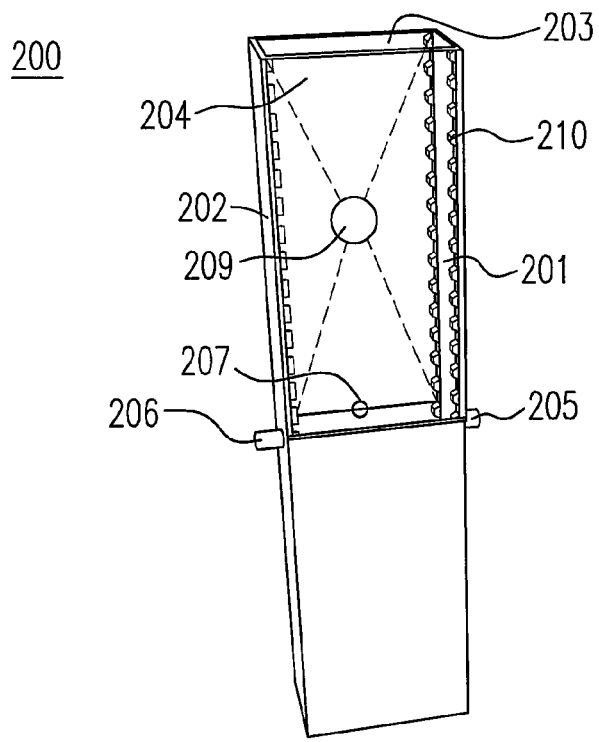

A perspective schematic view and a back perspective view vehicle of the present invention are respectively shown in FIGS. 2(a) and 2(b). The vehicle 200 includes at least one moving device 210 connected to the supporting frame 121 for fixing the supporting portion and vertically moving the supporting frame 121. The vehicle 200 is a cuboid having a first side 201, a second side 202, a third side 203 and a fourth side 204, wherein the first side 201, the second side 202, the third side 203 and the fourth side 204 corresponds to the first lateral 111, the second lateral 112, the third lateral 113 and the fourth lateral 114 of the tank 110. An optical fiber light source 205 generating a first light is configured on the first side 201 of the vehicle 200, and the first light is a UV-VIR-VIS light. An optical fiber sensor 206, 207 are respectively configured on the second side 202 and the third side 203, which receiving the UV-VIR-VIS light generated from the optical fiber light source 205. A matrix optical sensor 209 is further disposed on the third side 203 and a surface source 208 is further disposed on the fourth side 204. The surface source 208 generates a visible light and is received by the matrix optical sensor 209. A clean water entrance 221 and a waste water entrance 222 is configured above the vehicle 200 to be filled with a clean water and a waste water into the tank 110.

Figure 3:
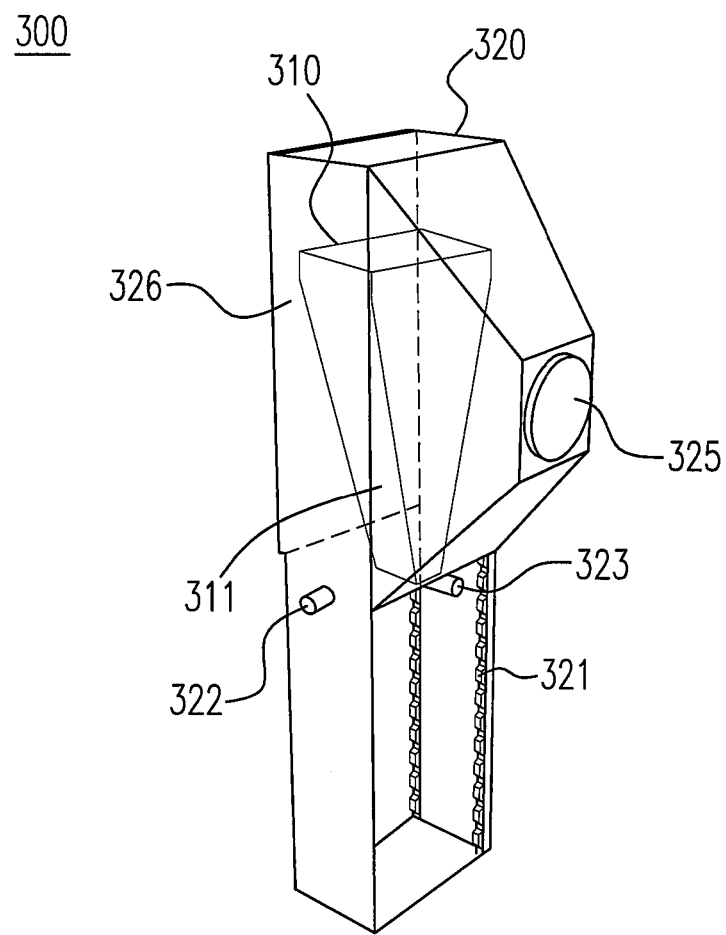
FIG. 3 shows a schematic diagram of the water tank combined with the vehicle of the present invention.

A schematic diagram of the water tank combined with the vehicle of the present invention is shown in FIG. 3. In the measuring device 300 in FIG. 3, the supporting frame 121 (not shown in FIG. 3) of the water tank 310 is connected to the moving device 321 of the vehicle 320 for fixing and vertically moving the water tank 310. The moving device 321 of the measuring device 300 is a chain gear set or other device rendering the supporting portion and the vehicle 320 moved relatively.

Figure 4A:
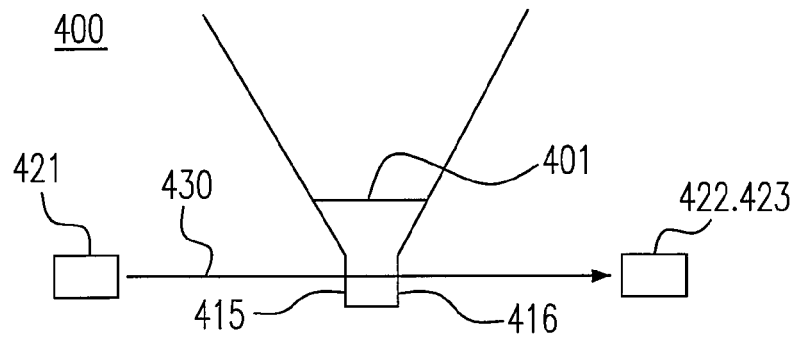
FIGS. 4(a) to 4(c) show the perspective view of optical analysis by using of the measuring device to measure the water of the present invention.
Figure 4B:
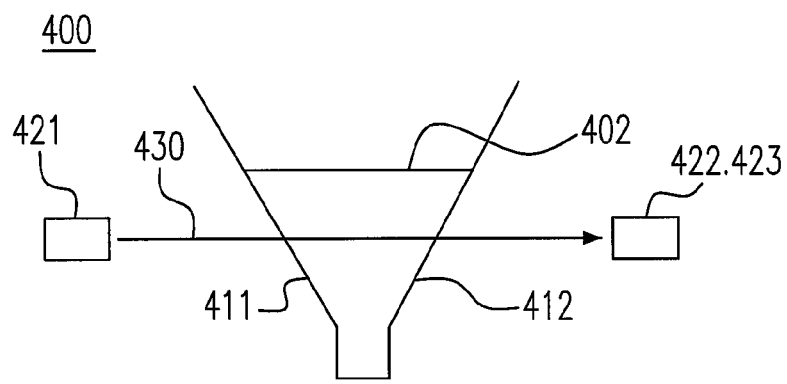
Figure 4C:
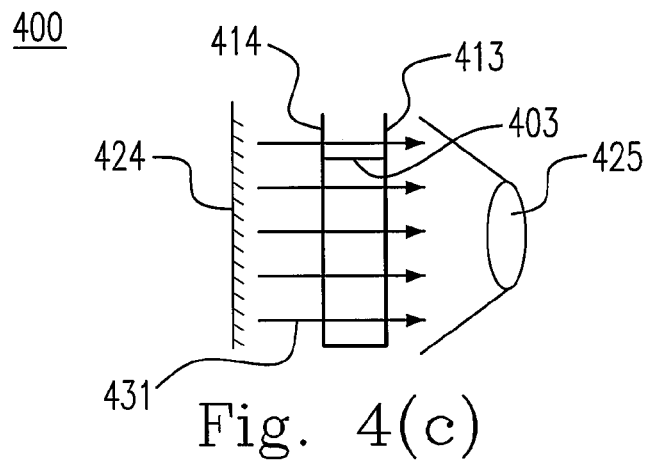

In water measurement, when the water level is at low water level 401 in the tank 440 of the water tank 310, as shown in FIG. 4(*a*), the UV-VIS-NIR light 430 generated from the optical fiber source 421 passes sequentially through the fifth lateral 415, the water and the sixth lateral 416 of the tank 400, and is received by the optical fiber sensor 422, 423. When the water level is at high water level 402 in the tank 440 of the water tank 310, as shown in FIG. 4(*b*), the moving device will move and render the water tank moved downward relative to the vehicle, to make the UV-VIS-NIR light 430 generated from the optical fiber source 421 passing sequentially through the first lateral 411, the water and the second lateral 412 of the tank 400, and received by the optical fiber sensor 422, 423. A height of the water level 403 is measured by the matrix optical sensor 425, as shown in FIG. 4(*c*). Under the condition, the visible light 431 generating from the surface source 424 on the vehicle 320 passes sequentially through the fourth lateral 414, the water and the third lateral 413 of the tank 400, and is received by the matrix optical sensor 425 to determine the height of the water level 403 in the tank 330. When a penetrability of the tank is not good, an ultrasonic device such as a sonicator or an ultrasonic oscillator configured on the outer wall can clean the tank by utilizing various frequencies.

The present invention uses the sensitive, accurate, speedy, no interference, micro-sampling and all system analysis characteristics that a UV-VIS-NIR spectrophotometer has to measuring the heavy metal and the concentration thereof. According to the spectrum property and the Beer-Lambert Law, the UV-VIS-NIR spectrophotometer can deal with the qualitative analysis and the quantitative analysis of the component and the concentration thereof in the water. Especially, the solubility substance exists in the waste water as a molecule form, different molecule form, functional group or chromophore will cause different absorbance spectrum. Therefore, the UV-VIS-NIR spectrophotometer can utilize the specific absorbance wavelength to identify an organic compound and the structure thereof to achieve the purpose of qualitative analysis of the component in the waste water. Most of the absorbance peak of the organic compound falls in infrared area and ultraviolet area, wherein the absorbance of the infrared area relates to the bonding resonance of the organic compound and the absorbance of the ultraviolet area relates to the functional group of the organic compound. The organic compound has many potential chromophores, wherein the chromophore and an auxochrome respectively become an electron acceptor and an electron donor when they combine to each other, to make the absorbance wavelength of the organic compound move forward to the long wavelength or increase the absorbance strength, and can produce a peak in the visible light area to qualitative analyze the component of the organic compound. In addition, the principle involved herein to quantitate the waste water is according to the Beer-Lambert Law. As the formula 1, the higher of the concentration of a component, the higher of the absorbance value caused by the concentration of the component. Hence, the quantitative analysis can use the absorbance value of the absorbance spectrum to reach the purpose of the quantitative component concentration in the waste water.

$$A=abc \quad \text{(formula 1)}$$

Wherein A is absorbance, a is molar absorptive coefficient, b is optical path length, and c is a concentration of a solution.

The present invention constructs a technique for measuring a component and the concentration thereof immediately of the water according to the principle of the above-captioned. The content of the technique mainly separates into three parts which are the construction of the spectrum data base of the water component, the construction of the poly-components qualitative and quantitative algorithm, and the identification in the laboratory and the factory. The strategy and method are described as follows:

1. The establishment of the spectrum data base of the water component.

In nature, whether a metal exists in a compound state or an ion state, they all difficult to degrade by organism to remove from the nature. When the metal enters into a tissue or an organ in the organism via food, it will cause a permanent damage to the fertility and the central nervous system. The metal for using in the different industries is different, for example, the copper is used as a dye or a fixing agent in the dyeing and finishing industry, the copper is produced by etching and acid picking in the PCB industry, and the chromium is used in increasing the hardness and corrosion resistance of the plating element in the galvanization industry. Accordingly, the present invention uses common metal such as copper, chromium, nickel and iron regard as a target of the heavy metal ion spectrum data base in the waste water. To construct the spectrum character of the heavy metal, the heavy metal is prepared in various concentrations and scanned the absorbance spectrum thereof for obtaining the absorbance wavelength, the characteristic wavelength and the absorbance coefficient, and to be a base of the poly-components qualitative and quantitative algorithm.

2. The poly-components qualitative and quantitative algorithm.

The analysis procedure of the poly-component algorithm uses the whole wavelength absorbance spectrum via data pre-treatment and noise removed, then measures the quality and quantity of components of the waste water. The analysis procedure of the poly-components algorithm mainly separates to three parts which including the pre-treatment of absorbance spectrum data, poly-component qualitative algorithm and the poly-components quantitative algorithm, and be described as follows:

The first part: the pre-treatment of absorbance spectrum data. Before entering the poly-component qualitative algorithm and the poly-component quantitative algorithm, need to set a range value of the absorbance spectrum by scanning the water. Then selecting a more meaningful spectrum data (i.e. the absorbance wave band of each component) to regard as a basis of follow-up algorithm.

The second part: the poly-component qualitative algorithm. According to the different component, the absorbance wave band thereof will be different. The poly-component qualitative algorithm utilizes the absorbance spectrum of all wave band scanning to compare with spectrum character data of the water which established by the step above-mentioned. The poly-component qualitative algorithm estimates the component existed in the water sample by scanning of the long wavelength to the short wavelength and obtained an absorbance thereof.

Furthermore, the poly-component qualitative algorithm then utilizes the spectrum scanning data of plurality of the dilution water (190~1100 nm absorbance) and the concentration of estimated component to establish a weight of each wavelength respective relative to the component in the water via a neural network, sifts the characteristic wavelength of each component through the weight proportion of each component to gauge and identify the component existed in the water.

The third part: the poly-component quantitative algorithm. A spectrogram of the water is a result of the component absorbs the UV-VIS-NIR in the water. Due to the component in the water has different absorbance ability to light which causing interference and competition between the components, and the variation of the raw materials used in the factory and the component of the waste water produced by the raw materials is not big. Therefore, the measuring device of the present invention establishes a relationship between the spectrum data and the component in the water by scanning plurality of waste water, obtaining a spectrum data via the different optical paths and the different dilution multiples, comparing the concentration of the water obtained by manual examination, then estimating by the neural network to develop a technique of measuring the component in the water.

3. The identification in the laboratory and the factory.

The identification procedure of the laboratory and the factory include two parts:

The first part: establishing an absorbance spectrum and an absorbance coefficient of the component in the water. Diluting the waste water sample in plural multiples and proceeding UV-VIS-NIR spectrum scanning and measuring a heavy metal, a suspended solid and a COD. Deducting the interference of UV-VIS-NIR absorbance spectrum produced by the suspended solid and the organic compound from the waste water sample to obtain the absorbance spectrum and absorbance of every component. Calculating a weight of the UV-VIS-NIR wave band of each component by neural network according to the concentration and the absorbance of the component which is known in the water.

The first part: establishing a synchronous solution method of the plurality of concentration of the component in the water.

Step 1: diluting the waste water of the factory in plurality dilution multiple and proceeding plurality scan of the UV-VIS-NIR absorbance spectrum continuously.

Step 2: measuring the concentration of the suspended solid in the diluted waste water sample by filtrating, and proceeding the scan of the UV-VIS-NIR absorbance spectrum.

Step 3: analyzing water quality of the raw materials needed by the procedure of the factory and the component may existed in the waste water.

Step 4: utilizing the spectrum scanning data of plurality diluted water sample to establish the characteristic wavelength of the component existed in the water via the weight studied neural network and the technique of spectrum analysis.

Step 5: analyzing the spectrum scanning data of plurality diluted original water to measure the property of the suspended solid and the spectrum wave band influenced by the suspended solid.

Step 6: accumulating a certain number of the water quality and the spectrum data, and establishing the UV-VIS-NIR absorbance spectrum and estimating the mode of the component concentration by neural network.

Step 7: if the result of the estimating mode is not good, repeats the procedure of the step 1, and accumulates enough data to increase the ability of the study and the estimation of the neural network.

Step 8: to maintain the measuring effectiveness of the mode, the estimation mode must be regulated and advised by the result of the regular sampling analysis when the procedure of the factory is changed.

Operating Procedures

1. The procedure of entering a clean water: the amount of the entered clean water is among 0.1~100 mL. The clean water is a deionized water.

2. The correcting procedure of the dark electric current.

3. The correcting procedure of the light source air: to gauge the strength of the light source.

4. The correcting procedure of the light source strength: the measured of the light source strength regards as a original light source strength and measuring a base line to gauge the stability of the measuring device.

5. The procedure of draining the clean water: draining the clean water to prepare the spectrum measuring of the waste water.

6. The procedure of entering the waste water: the amount of the entered waste water is among 0.1~100 mL. The amount of the clean water entered into the tank is according to the amount of the water sample and the multiple of the water sample wanted to dilute.

7. The procedure of measuring by the UV-VIS-NIR: when proceeding dilute procedure, the property dilution multiple must be found (absorbance<the largest value that an instrument can detect) then proceeding precipitation procedure. If the absorbance is bigger than the value that the instrument can detect, the water tank could be moved vertically to change the optical path or the waste water could be diluted by adding the clean water then detecting the absorbance at the same point, and let the last absorbance is smaller than the largest value that an instrument can detect. Measuring plurality of optical paths according to the dilution multiple, plurality of dilution multiple continuously or the precipitation spectrums of the waste water by the UV-VIS-NIR. The amount and the height of the dilution waste water is obtained by a matrix optical sensor such as the charge-coupled device (CCD) or the complementary metal-oxide-semiconductor (CMOS) of the video camera. The highest position of the water tank is also gauged by the matrix optical sensor. Different dilution multiples have different heights of the water level, in other words, the moving of the tank is related to the height of the water level.

8. The procedure of draining the waster water.

9. The procedure of cleaning: let the tank be entered the clean water, moved vertically once and scanned simultaneously to measure the light source strength of each path. The tank will re-clean when the light source strength is less than the 95% of the original light source strength and stop cleaning procedure when the light source strength is more than the 95% of the original light source strength.

Embodiment 1

A copper-contained liquid sample is prepared to a concentration of 50 ppm, and put the 50 ppm copper-contained liquid sample into the tank. At first, the 50 ppm copper-contained liquid sample is proceeded a UV-VIR-NIS spectrum measurement at the 190~400 nm, 400~700 nm and 700~1100 nm wavelength. Then, the 50 ppm copper-contained liquid sample is diluted to 25 ppm, 10 ppm, 5 ppm and 1 ppm, respectively. At last, the 50 ppm copper-contained liquid sample is proceeded the UV-VIR-NIS spectrum measurement at the wavelength above-mentioned, respectively. The result is shown in FIGS. 5(*a*), 5(*b*) and 5(*c*).

Figure 5A:
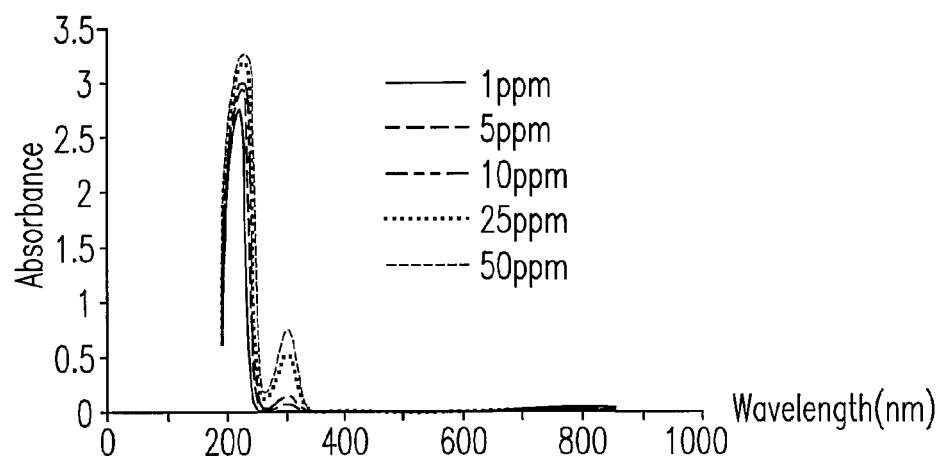
FIGS. 5(a), 5(b) and 5(c) show the spectrum database of the copper heavy metal.
Figure 5B:
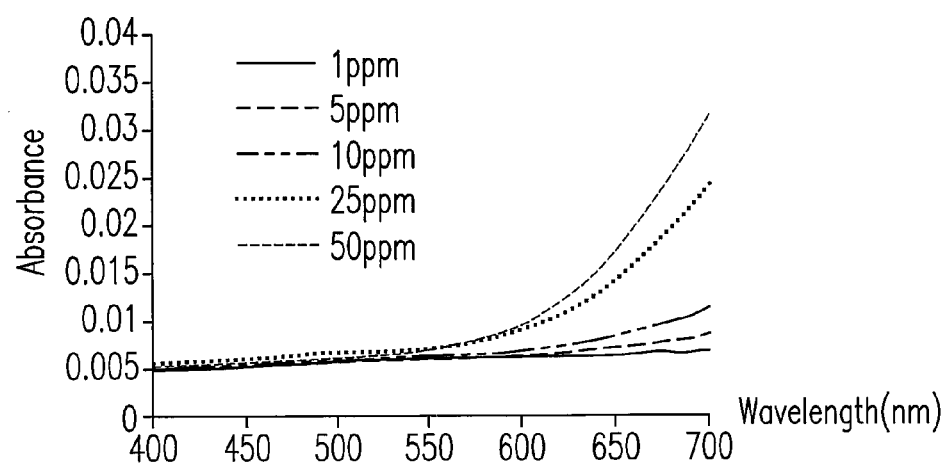
Figure 5C:
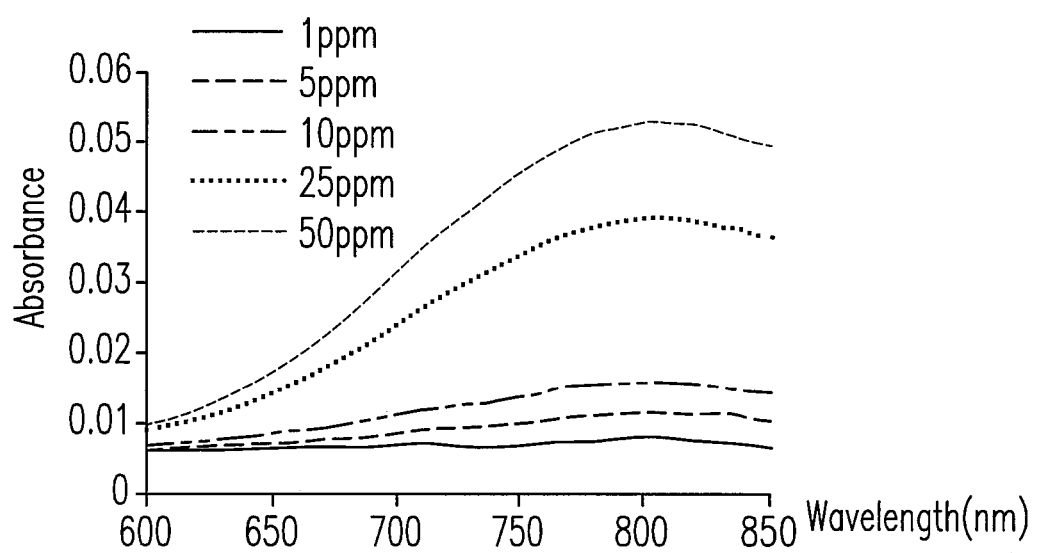

The established result of the copper heavy metal spectrum database: the copper heavy metal is measure in plurality of concentration (1 ppm, 5 ppm, 10 ppm, 25 ppm and 50 ppm) and the result is shown in FIG. 5(*c*). When the optical path is 5 cm, the absorbance peak of the copper heavy metal will be sited at 800 nm and 805 nm.

Embodiment 2

A nickel-contained liquid sample is prepared to a concentration of 50 ppm, and put the 50 ppm nickel-contained liquid sample into the tank. At first, the 50 ppm nickel-contained liquid sample is proceeded a UV-VIR-NIS spectrum measurement at the 190~400 nm, 400~700 nm and 700~1100 nm wavelength. Then, the 50 ppm nickel-contained liquid sample is diluted to 25 ppm, 10 ppm, 5 ppm and 1 ppm, respectively. At last, the 50 ppm nickel-contained liquid sample is proceeded the UV-VIR-NIS spectrum measurement at the wavelength above-mentioned, respectively. The result is shown in FIGS. 6(*a*), 6(*b*) and 6(*c*).

Figure 6A:
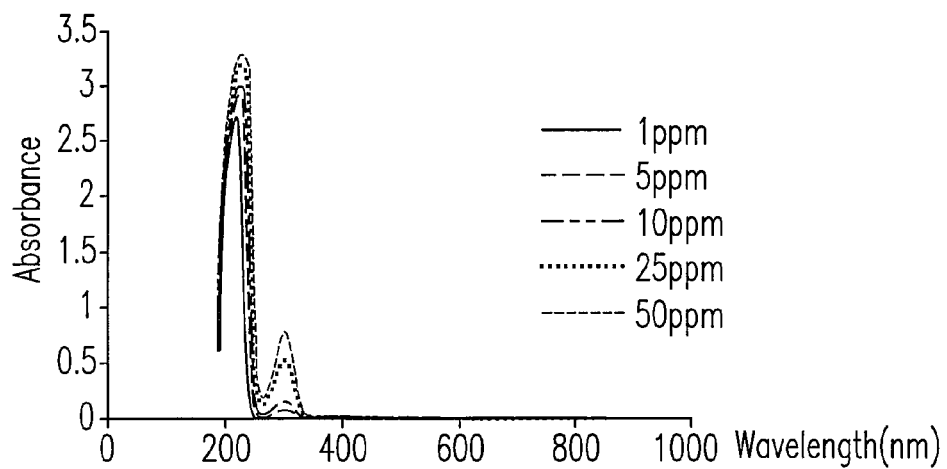
FIGS. 6(a), 6(b) and 6(c) show the spectrum database of the nickel metal.
Figure 6B:
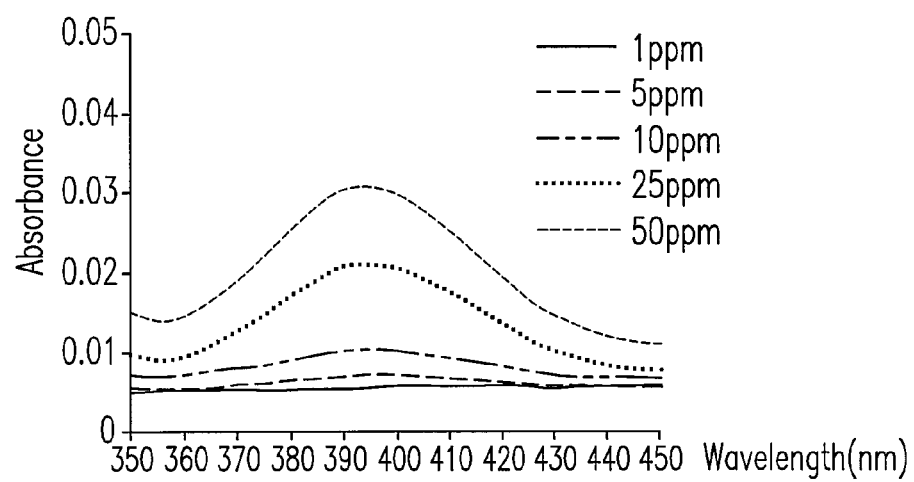
Figure 6C:
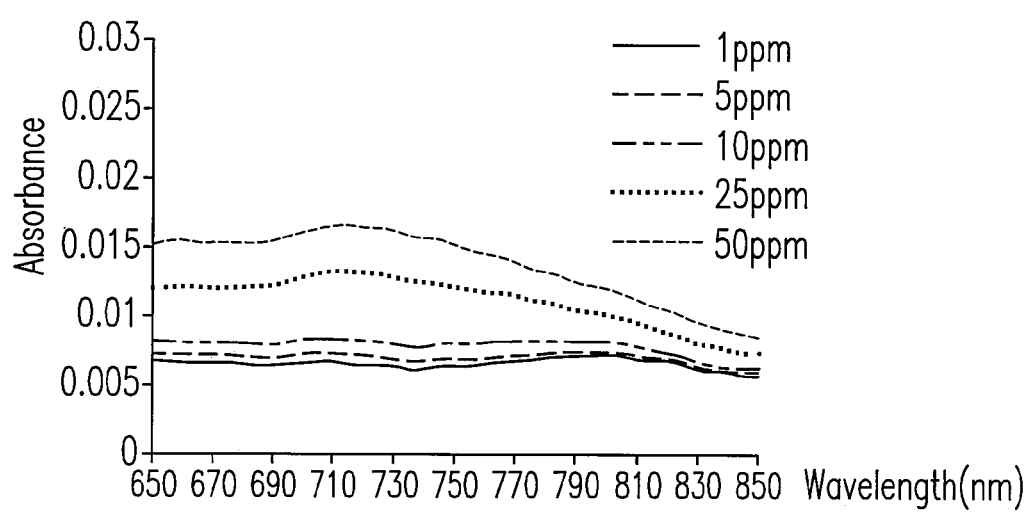

The established result of the nickel heavy metal spectrum database: the nickel heavy metal is measure in plurality of concentration (1 ppm, 5 ppm, 10 ppm, 25 ppm and 50 ppm) and the result is shown in FIGS. 6(*b*) and 6(*c*). When the optical path is 5 cm, the absorbance peak of the nickel heavy metal will be sited at 390 nm and among 705 nm to 710 nm.

Embodiment 3

A chromium-contained liquid sample is prepared to a concentration of 50 ppm, and put the 50 ppm chromium-contained liquid sample into the tank. At first, the 50 ppm chromium-contained liquid sample is proceeded a UV-VIR-NIS spectrum measurement at the 190~400 nm, 400~700 nm and 700 1100 nm wavelength. Then, the 50 ppm chromium-contained liquid sample is diluted to 25 ppm, 10 ppm, 5 ppm and 1 ppm, respectively. At last, the 50 ppm chromium-contained liquid sample is proceeded the UV-VIR-NIS spectrum measurement at the wavelength above-mentioned, respectively. The result is shown in FIGS. 7(*a*), 7(*b*) and 7(*c*).

Figure 7A:
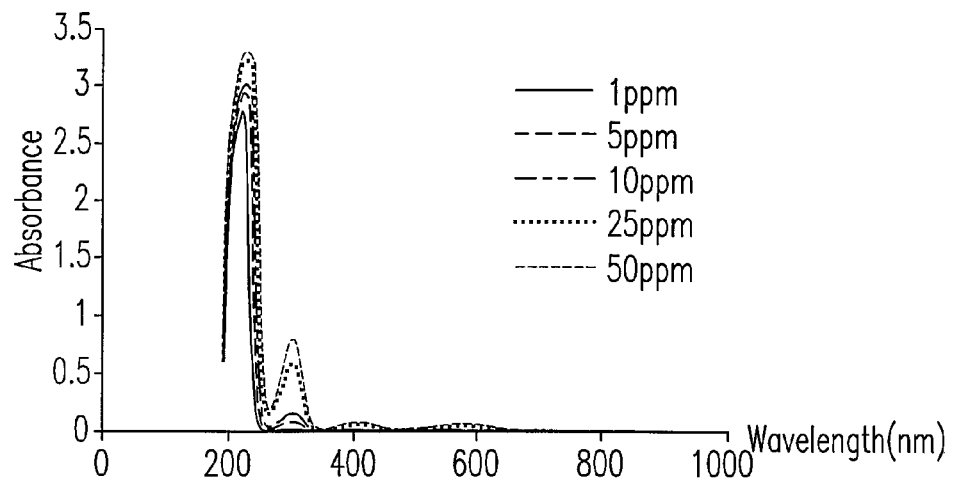
FIGS. 7(a), 7(b) and 7(c) show the spectrum database of the chromium heavy metal.
Figure 7B:
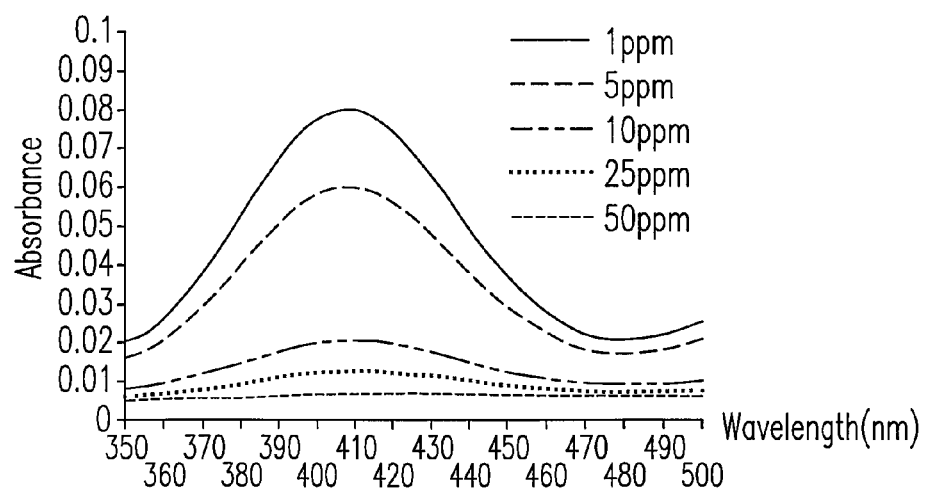
Figure 7C:
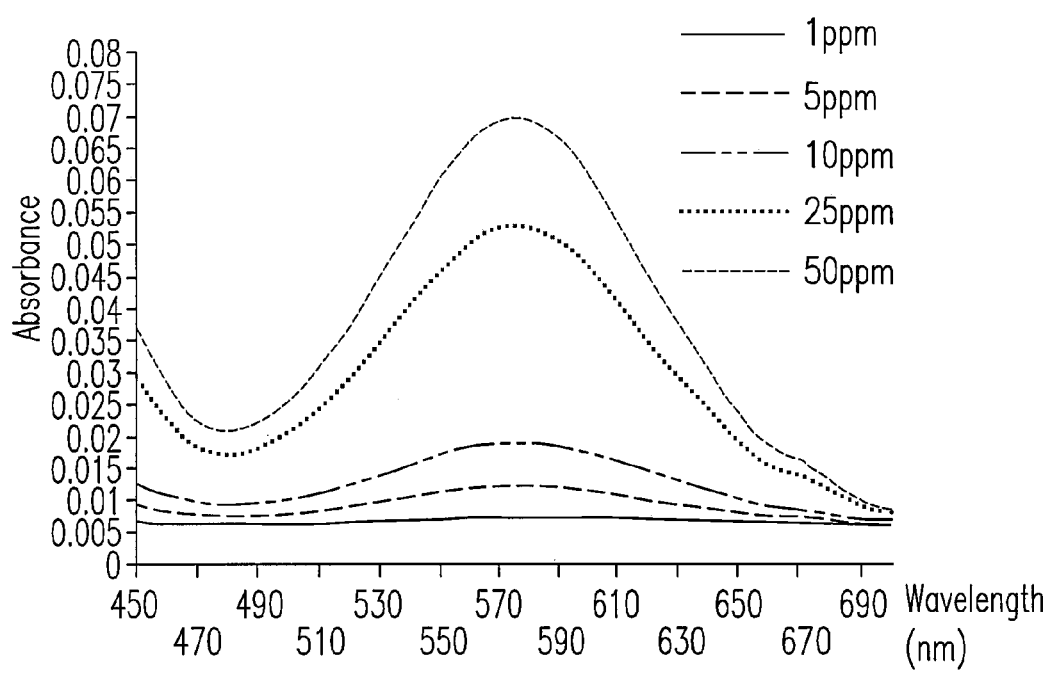

The established result of the chromium heavy metal spectrum database: the chromium heavy metal is measure in plurality of concentration (1 ppm, 5 ppm, 10 ppm, 25 ppm and 50 ppm) and the result is shown in FIGS. 7(*b*) and 7(*c*). When the optical path is 5 cm, the absorbance peak of the chromium heavy metal will be sited at 410 nm 575 nm.

Embodiment 4

Figure 8:
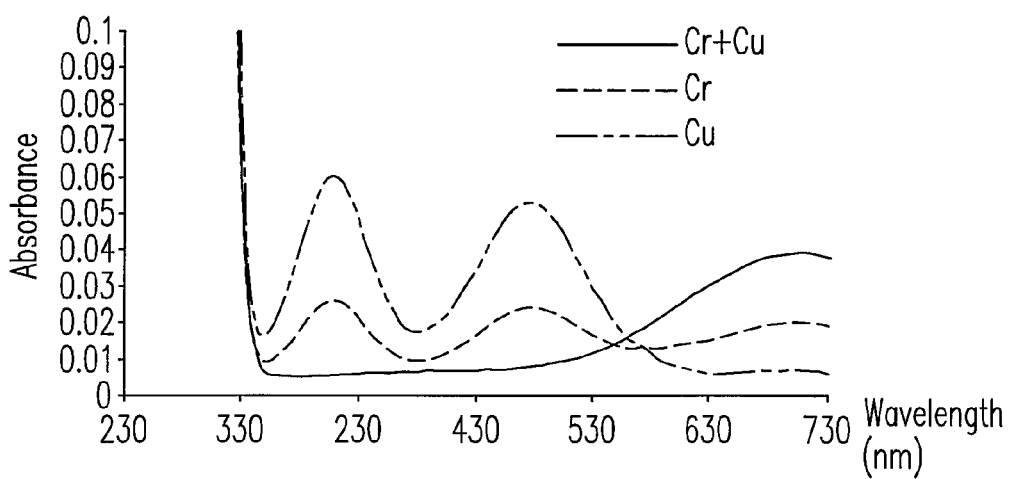
FIG. 8 shows the spectrum scanning of mixture water sample of the copper and the chromium heavy metal.

The chromium and the copper heavy metal mixed water sample spectrum: as shown in FIG. 8, it is found that there are two wave peaks sited at 410 nm and 575 nm. Hence, it can be determined that the chromium heavy metal is existed in this water sample. Furthermore, the absorbance of the water sample is raised with increasing wavelength after 650 nm. Accordingly, it can be determined that the copper heavy metal is existed in this water sample.

Embodiment 5

Figure 9:
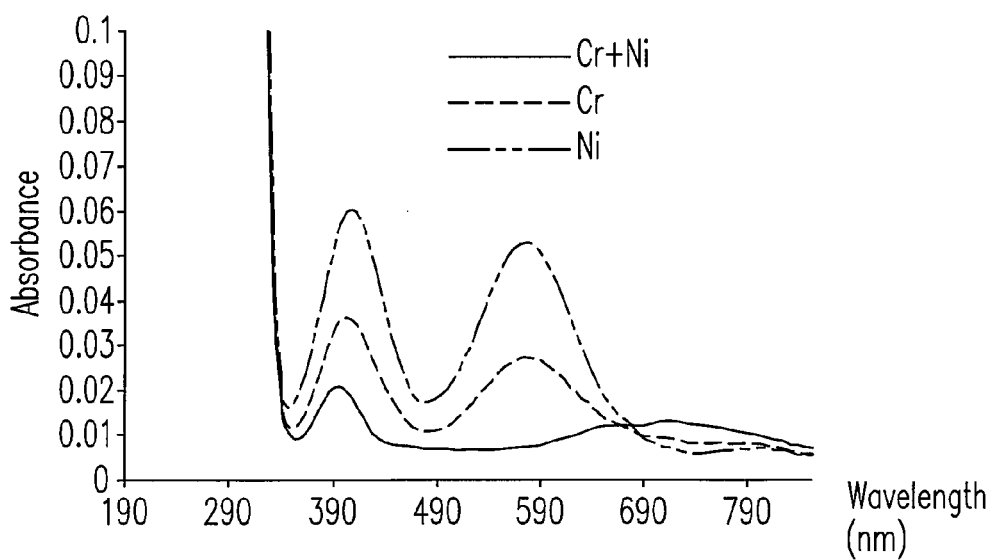
FIG. 9 shows the spectrum scanning of mixture water sample of the nickel and the chromium heavy metal.

The chromium and the nickel heavy metal mixed water sample spectrum: as shown in FIG. 9, it is found that there are two wave peaks sited at 410 nm and 575 nm. Hence, it can be determined that the chromium heavy metal is existed in this water sample. Furthermore, there is one wave peak sited at 390 nm, hence, it can be determined that the nickel heavy metal is existed in this water sample. However, the absorbance of the water sample is decreased with increasing wavelength after 690 nm. Accordingly, it can be determined that the copper heavy metal is not existed in this water sample.

Embodiment 6

Figure 10:
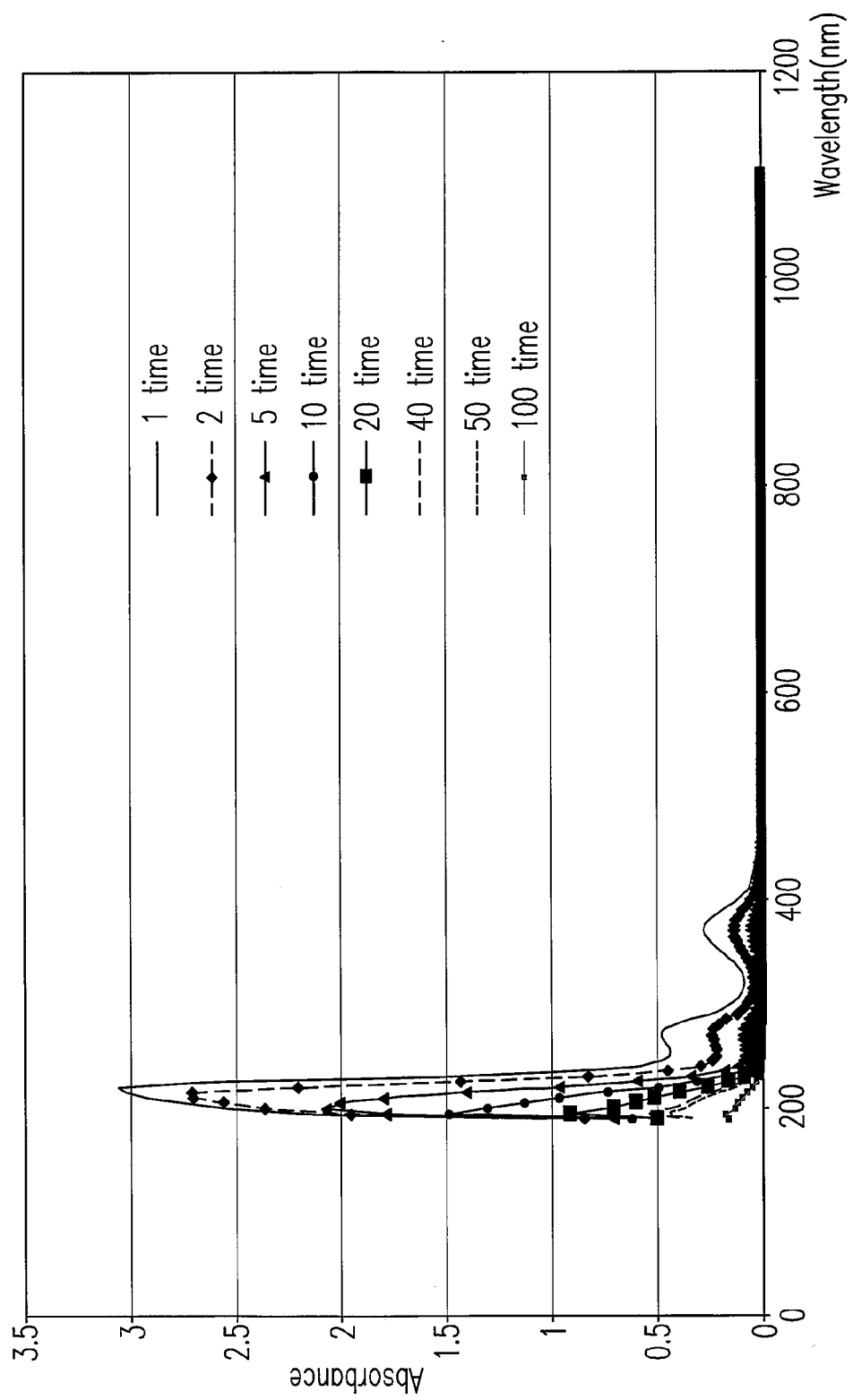
FIG. 10 shows the spectrum scanning of mixture water sample of the electroplating industry.

The spectrum of the waste water of the electroplating factory: FIG. 10 shows the result of scanning spectrum of plurality of dilution multiple of the waste water. It is found that there are two wave peaks sited at 275 nm and 375 nm, and can be determined that there are aldehydes and zinc heavy metal existed in the waste water sample according to the spectrum database. However, there does not have other bigger wave peak so that it can be determined that there is no other component existed in the waste water sample.

Embodiment 7

Figure 11:
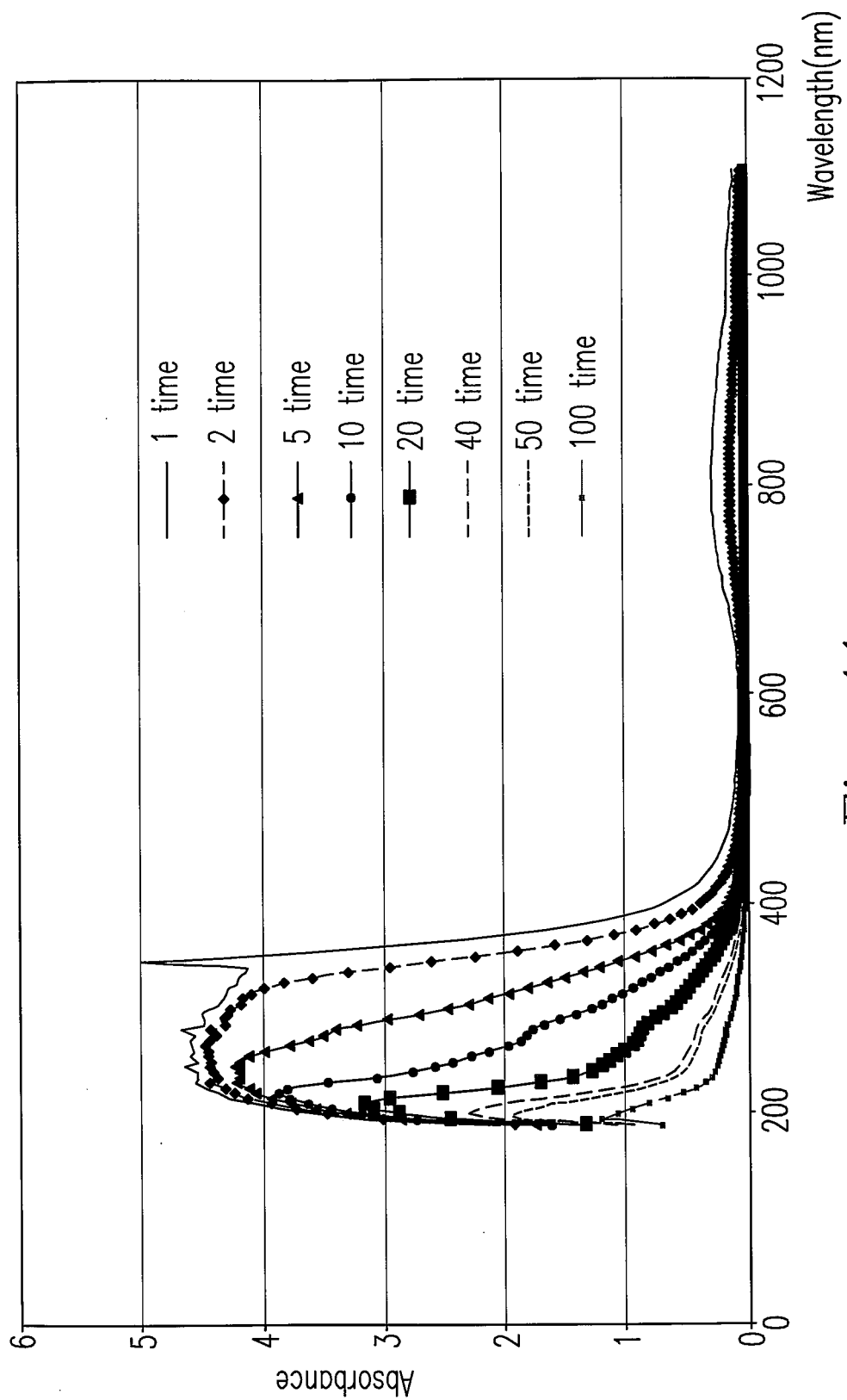
FIG. 11 shows the spectrum scanning of mixture water sample of the print circuit board industry.

The spectrum of the waste water of the PCB factory: FIG. 11 shows the result of scanning spectrum of plurality of dilution multiple of the waste water. It is found that there are three wave peaks sited at 280 nm, 400 nm and 800 nm, and can be determined that there are aldehydes, zinc heavy metal and copper heavy metal existed in the waste water sample according to the spectrum database. However, there does not have other bigger wave peak so that it can be determined that there is no other component existed in the waste water sample.

There are further embodiments provided as follows.

Embodiment 1. In a measuring device, including: a tank, a supporting portion, a vehicle, a first light source and a first measuring element. The tank has a first and a second laterals including a first and a second virtual extensions respectively, for filling therein a water wherein the first and the second laterals are light-permeable and oppositely configured, and the first and the second virtual extensions intersects to form an angle. The supporting portion has at least one supporting frame connected to the tank. The vehicle has at least one moving device connected to the supporting portion for fixing the supporting portion and vertically moving the supporting portion. The first light source is configured outside the tank and generating a first light toward to the first lateral. The first measuring element is configured outside the tank and facing the second lateral for receiving the first light passing sequentially through the first lateral, the water and the second lateral to measure the water.

Embodiment 2. In the measuring device according to the above-mentioned embodiment 1, the tank further includes a third lateral being light-permeable and connected to the first lateral and the second lateral. The measuring device further includes a second measuring element configured outside the tank and facing the third lateral. The second measuring element receives the first light in the water for measuring the water.

Embodiment 3. In the measuring device according to the above-mentioned embodiment 2, the tank further includes a fourth lateral being light permeable and parallel to the third lateral. The measuring device further includes a second light source configured outside the tank. The second light source generates a second light and facing the fourth lateral. A third measuring element is configured out side the tank and facing the third lateral. When the first light is not emitted, the third measuring element receives the second light passing sequentially through the fourth lateral, the water and the third lateral to measure a parameter of the water being selected from a group consisting of a height of the water level, a concentration of a suspended solid, a sedimentation rate of a suspended solid and a combination thereof.

Embodiment 4. In the measuring device according to the above-mentioned embodiment 1, the tank further includes a fifth and a sixth laterals parallel to each other. The fifth lateral is connected with the first lateral. The sixth lateral is connected with the second lateral. The intersection formed by the virtual extensions of the first lateral and the second lateral is sited between the fifth lateral and the sixth lateral. When the tank is moved to a position that the first light source faces to the fifth lateral, the first measuring element receives the first light.

Embodiment 5. In a measuring device, including: a tank filled with a fluid sample. The tank has at least two optical paths for measuring a property of the fluid sample through the at least two optical paths.

Embodiment 6. In the measuring device according to the above-mentioned embodiment 5, the tank has a cross-section area being changed along a length direction thereof.

Embodiment 7. In the measuring device according to the above-mentioned embodiment 6, the tank has a light-permeable material and is an inverted triangular prism having a bottom to make the measuring device have plural optical paths. The bottom is connected to a cuboid. The cuboid is light-permeable and has a smallest optical path for the measuring device.

Embodiment 8. In the measuring device according to the above-mentioned embodiment 7, the tank is a main tank and the inverted triangular prism has an outer wall. The measuring device further includes: an air tank configured above the main tank. An opaque black tank is configured above the air tank. The air tank and the opaque black tank is used for proceed a calibration of a light source intensity and a light sensor. An ultrasonic device is configured on the outer wall. The ultrasonic device cleans the main tank and mixes the fluid sample therein by utilizing various frequencies.

Embodiment 9. In the measuring device according to the above-mentioned embodiment 5, further including: a supporting portion supporting the tank. A vehicle having at least one moving device connected to the supporting portion for fixing the same and vertically moving the same.

Embodiment 10. In a fluid sample measuring process, including steps of: (a) measuring a change of a spectral intensity of the fluid sample to obtain an absorbance. (b) The absorbance is determined whether the absorbance falls in an error tolerance. If not, at least one of diluting the fluid sample and changing an optical length is/are performed. (c) The steps (a) and (b) are repeated until the absorbance falls in the error tolerance.

Embodiment 11. In the fluid sample measuring process according to the above-mentioned embodiment 10, the step (a) further includes the step of measuring the change of the spectral intensity of the fluid sample via at least two light with different wavelengths from a lighting device to obtain the absorbance.

Embodiment 12. In the fluid sample measuring process according to the above-mentioned embodiment 11, further including a step of: (a0) diluting the fluid sample and scanning the fluid sample by one of the lighting device and an optical fiber.

Embodiment 13. In the fluid sample measuring process according to the above-mentioned embodiment 11, the light device is a UV-VIS-NIR spectrum equipment.

Embodiment 14. In the fluid sample measuring process according to the above-mentioned embodiment 10, the fluid sample measuring process is used in measuring a parameter of a water of being one selected from a group consisting of a heavy metal concentration, a suspended particulate concentration, an organic concentration, a chemical oxygen demand and a combination thereof.

While the invention has been described in terms of what is presently considered to be the most practical and preferred embodiments, it is to be understood that the invention needs not be limited to the disclosed embodiments. Therefore, it is intended to cover various modifications and similar configuration included within the spirit and scope of the appended claims, which are to be accorded with the broadest interpretation so as to encompass all such modifications and similar structures.

REFERENCES

U.S. Pat. No. 5,244,634 (Nov. 29, 1991)
U.S. Patent No. 2009/0263907 A1 (Aug. 27, 2007)

What is claimed is:

1. A measuring device, comprising:
a tank having a first and a second laterals including a first and a second virtual extensions respectively, for filling therein a water wherein the first and the second laterals are light-permeable and oppositely configured, and the first and the second virtual extensions intersect to form an angle;
a supporting portion having at least one supporting frame connected to the tank;
a vehicle having at least one moving device connected to the supporting portion for fixing the supporting portion and vertically moving the supporting portion;
a first light source configured outside the tank and generating a first light toward to the first lateral; and
a first measuring element configured outside the tank and facing the second lateral for receiving the first light passing sequentially through the first lateral, the water and the second lateral to measure the water.

2. The measuring device as claimed in claim 1, wherein the tank further comprises a third lateral being light-permeable and connected to the first lateral and the second lateral, the measuring device further comprises a second measuring element configured outside the tank and facing the third lateral, and the second measuring element receives the first light in the water for measuring the water.

3. The measuring device as claimed in claim 2, wherein the tank further comprises a fourth lateral being light permeable and parallel to the third lateral, the measuring device further comprises a second light source configured outside the tank, generating a second light and facing the fourth lateral, and a third measuring element configured outside the tank and facing the third lateral, when the first light is not emitted, the third measuring element receives the second light passing sequentially through the fourth lateral, the water and the third lateral to measure a parameter of the water being selected from a group consisting of a height of the water level, a concentration of a suspended solid, a sedimentation rate of a suspended solid and a combination thereof.

4. The measuring device as claimed in claim 1, wherein the tank further comprises a fifth and a sixth laterals parallel to each other, the fifth lateral is connected with the first lateral, the sixth lateral is connected with the second lateral, the intersection formed by the virtual extensions of the first lateral and the second lateral is sited between the fifth lateral and the sixth lateral, and when the tank is moved to a position that the first light source faces the fifth lateral, the first measuring element receives the first light.

* * * * *